(12) United States Patent
Cavali

(10) Patent No.: US 9,028,532 B2
(45) Date of Patent: May 12, 2015

(54) FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILITIES

(76) Inventor: Paulo Tadeu Maia Cavali, Nova Conceicao (BR)

( * ) Notice: Subject to any disclaimer, the term of this patent is extended or adjusted under 35 U.S.C. 154(b) by 726 days.

(21) Appl. No.: 12/678,440

(22) PCT Filed: Dec. 7, 2007

(86) PCT No.: PCT/BR2007/000339
§ 371 (c)(1),
(2), (4) Date: Mar. 16, 2010

(87) PCT Pub. No.: WO2009/036541
PCT Pub. Date: Mar. 26, 2009

(65) Prior Publication Data
US 2010/0211103 A1    Aug. 19, 2010

(30) Foreign Application Priority Data

Sep. 21, 2007 (BR) .............................. 013070062474

(51) Int. Cl.
*A61B 17/70* (2006.01)
(52) U.S. Cl.
CPC .......... *A61B 17/7026* (2013.01); *A61B 17/701* (2013.01); *A61B 17/7032* (2013.01)
(58) Field of Classification Search
CPC .......... A61B 17/7049; A61B 17/7053; A61B 17/705; A61B 17/701; A61B 17/7005; A61B 17/7019; A61B 17/7026; A61B 17/7031; A61B 17/7032; A61B 17/7034

USPC ............................................ 606/61, 250–261
See application file for complete search history.

(56) References Cited

U.S. PATENT DOCUMENTS

| | | | |
|---|---|---|---|
| 2006/0064090 A1* | 3/2006 | Park ................................ | 606/61 |
| 2006/0149228 A1* | 7/2006 | Schlapfer et al. ............... | 606/61 |
| 2006/0229608 A1* | 10/2006 | Foster et al. .................... | 606/61 |

* cited by examiner

*Primary Examiner* — Ellen C Hammond
*Assistant Examiner* — Christina Negrellirodrigue
(74) *Attorney, Agent, or Firm* — Galbreath Law Offices, P.C.; John A. Galbreath

(57) ABSTRACT

Flexible, sliding, dynamic implant system, for selective stabilization and correction of the vertebral column deformities and instabilities is constituted of a set is constituted by a set of flexible vertebral implants, which are articulated, sliding and dynamic (1) that belongs to the prosthetic and implants medicine field, constituted of two linear parallel sequences of U-shaped supports or platforms (3) where each pair of the sequence is connected with selective mobility to pedicular screws (4) fixed, also in parity, in the due posterior bony portion (5) of each vertebra (6) two thin, continue and flexible metallic blades (8) are coupled between the edges (lateral portion of the platforms with tracks (7) which belong to each U-shaped support. The inferior thin blade (8) is a fixed to the first U-shaped support (3) which corresponds to the first inferior vertebra (6) of the vertebral portion to be implanted. The flexible thin blade (8) is, on its turn, fixed on the upper vertebra platform in a way that it is blocked in only one extremity, thus with the free internal extremity causing the blades to slide in postural flex condition or any other movement requested to the extension of the implanted vertebral column (2).

5 Claims, 5 Drawing Sheets

FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILITIES

FIELD IF THE INVENTION

The present privilege of invention patent relates to the field of prosthetic devices and implants for medicine. Its object is a set of internal articulated and flexible implants to be implanted next to the patient's vertebral column. It is recommended for the vertebral column surgical treatment in the case of fractures, vertebral deformities, degenerative illnesses, tumors of the vertebral column among other typical problems. It allows the patient to keep attended column mobility with greater comfort in his/her rehabilitation and treatment processes.

We have in the patent request, therefore, a new system of implants applied to the vertebral column, which project favors and supports the column movement after its implantation in a way to prevent exceeding forces to be applied on the vertebral column causing any kind of injury or damage. It has been conceived with intelligent and original constructive lay out, with the aim to assure that the patient has a choice of treatment and rehabilitation with a more comfortable experience.

The patent request presents an innovative internal implant system that is applied to the vertebrae with low cost for its industrial feasibility, considering safety requirements, robustness, comfort and simplicity, reaffirming its utilitarian practicality, giving the user patient freedom and option of a safe choice in the rehabilitation orthopedic surgery field, with improved possibilities and benefits, becoming a specific model of great expectation for this field of medicine.

BACKGROUND OF THE INVENTION

The correction of vertebral deformities in human beings as scoliosis, has a procedure that is known in the medical means as "gold standard" and uses implants that are fixed in the vertebrae with the use of pedicular screws (or hooks), which are assembled by a pair of cylindrical and rigid metallic connecting rods, producing vertebral alignment according to the alignment of the rigid rods.

Each portion of the implant (pedicular screws) is fixed to each vertebra or set of vertebrae and rigidly connected to the rod, in such way that after the deformity correction the column remains aligned according to the pre-modeling and positioning of the rigid rods. This standard procedure transforms a vertebral "twisted" (with scoliosis) column that presents mobility, into a "straight" (aligned) vertebral column, rigid, though. That is, without the natural mobility and flexibility.

This kind of vertebral column fixation pattern is also used in fracture related problems, degenerative illnesses and tumors of the vertebral column.

Deficient Points of the State of the Current Technique

The traditional system of implants disadvantage is regarding the loss of natural mobility and flexibility by the operated section of the vertebral column, causing the patient's trunk to move in a limited way and, as a consequence of this mobility loss, in the medium and long term, vertebral segments that are adjacent to the fixation place are subject to degeneration of intervertebral discs and facet joints, provoking premature arthroses, vertebral pain, not to mention huge discomfort.

The "destruction" of some anatomical structures is necessary for the implant of the traditional current system, which provokes a certain partial mutilation of the operated patient's column.

Another important inconvenience of the traditional procedure of vertebral implant relates to the loss of vertebral growth and development in the columns of patients in their growth period (young/in development).

INVENTION SUMMARY

The purpose of getting a new vertebral column applied implant system that corrects the inconveniences pointed out, with the aim of presenting almost all the natural degrees of mobility of a vertebral column, led the inventor with notorious sectorial knowledge to idealize, project and develop the object of the present patent, entitled "FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILIDADES", which conceives an implant system for stabilization and correction of the vertebral column that uses column connected implants to correct and stabilize it, keeping, however, the maximum possible movement only limiting it in the deformity or instability plans. This new vertebral column implant system also allows application on "growing columns" (immature patients) without compromising the vertebral development maintenance and without destroying any vertebral column anatomical structure, keeping it intact.

With the innovative implant system the vertebral column submitted to the implant, keeps almost the totality of the physiological movements in many plans, considered normal, which allows the column flexion and extension, and still allows the right and left lateral inclination, rotation or twist (right and left) as well as composed and complex movements (movements in two or more plans).

For the new implantation and stabilization technique accomplishment three types of considerations are taken into account:

Type 1: Fixation implants (anchorage) to the vertebra with the use of pedicular screws which are already available in the market.

Type 2: U-shaped fasteners or platforms are fixation implants connected to the screws' heads which also work as platforms that have internal tracks for blade sliding. The platform connections with the respective screw heads are made with the use of a poli-axial articulation which allows rotation and movement in many plans. The platforms can also have lateral connections which allow its lateralization in relation to the pedicular screw.

Type 3: Flexibel blades: These implants are made of one or two sets of two flexible blades which slide between themselves inside implant 2 head tracks. These sets substitute the clinical rigid bars of system that are already in the market. Such blade sets are put together (joined) on both sides of the column around the spinal proves in such way that for each side of the assembly at least two blades are connected to the platforms that are fixed to the screws.

The flexible blades can be straight pre-molded in kyphosis or lordosis.

The length of each blade is always smaller than the total desired fixation to allow that the blades slide between each other and one over the other.

The set of sliding flexible blades produces a correction of the lateral deformity (scoliosis) and at the same time allows the vertebral column movements of flex-extension and rotation in the instrumented vertebral segment, apart from allowing that, in immature columns (children and adolescents), it allows the growth and development to continue normally in the vertebral column.

The new vertebral implant system which is the aim of this patent has its project based on the movement that is produced by the blades flexibility and sliding which makes it possible to shorten and stretch the column with the use of the poli-axial mobility on track-articulated platforms over the screws' heads.

The new implants instrumentation is applied by the fixation of one of the blades in only one platform on the extremity and the fixation of another blade on the opposite extremity in such a way that each blade is blocked in only one extremity allowing them to slide between each other during the vertebral column movement. Thus, the blades' internal extremities are free to slide between each other.

The blades are connected to the intermediate poly-axial platforms (U-shaped fasteners) by tracks that allow a guided slide of the blades, therefore, the application of this newly shown implant allows the correction of vertebral deformities, keeps the vertebral column movement, and allows the vertebral column growth when applied to immature patients (children and adolescents in development/growth).

This new implant system can furthermore to be used in the stabilization of other vertebral column illnesses or problems as degenerative breaking illnesses and metabolic illnesses.

The innovations can be translated in:
1—Sets of flexible blades substituting the rigid rods.
2—Sliding between the flexible blades.
3—Platforms with internal tracks articulated with the pedicular screws' head to allow the blades to slide. The platform mobility degree or angulation in relation to the pedicular screw can be selectively defined and/or be blocked according to the deformity or illness to be treated.
4—Rings or gloves (S-shaped limiting fastener) along the blades to keep contact and to prevent the separation between blades and thus lead (to guide) its movements.
5—Metallic materials (titanium) or carbon-made blades. Being those straight or pre-molded in kyphosis or lordosis.

The new vertebral implant system that was developed with this new technique is understandably simple, being, therefore, feasible and achieving excellent practical and functional results and incorporating a simple, original and innovative technology.

The innovative vertebral implants system is produced with inert and non-toxic raw-material and offers users functional quality and robustness having great success expectations in the implant's procedure and usage.

BRIEF DESCRIPTION OF THE DRAWINGS

For a better understanding of how the "FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILIDADES" here claimed works, some illustrative drawings are presented herewith:

FIG. 6—Shows a view of a detail of the linear sequence of elements of the articulated vertebral implants components for stabilization and correction of the vertebral column deformities and instabilities, where we see: articulated vertebral implants (1), U-shaped supports or platforms (3), pedicular screw (4), lateral portion of the platform or edge (7), flexible thin blade (8), S-shaped fastener or glove (9) and (10).

FIG. 7—Shows a view in supero-posterior perspective of the double linear sequence of the vertebral implant's component elements of the vertebral implant system articulated for stabilization and correction of the vertebral column deformities exposing a postural flexion condition, where we see: articulated vertebral implants (1), U-shaped supports or platforms (3), pedicular screw (4), lateral portion of the platform or edge (7), flexible thin blade (8), metallic glove (10).

FIG. 8—Shows an enlarged view of the detail of a linear sequence of elements of the components of the vertebral implant system articulated for stabilization and correction of the vertebral column deformities exposing a postural flexion condition where we see: articulated vertebral implants (1), vertebral column (2), pedicular screw (4), vertebra (6), lateral portion of the platform or edge (7), flexible thin blade (8).

DETAILED DESCRIPTION OF THE INVENTION

Figure 1:
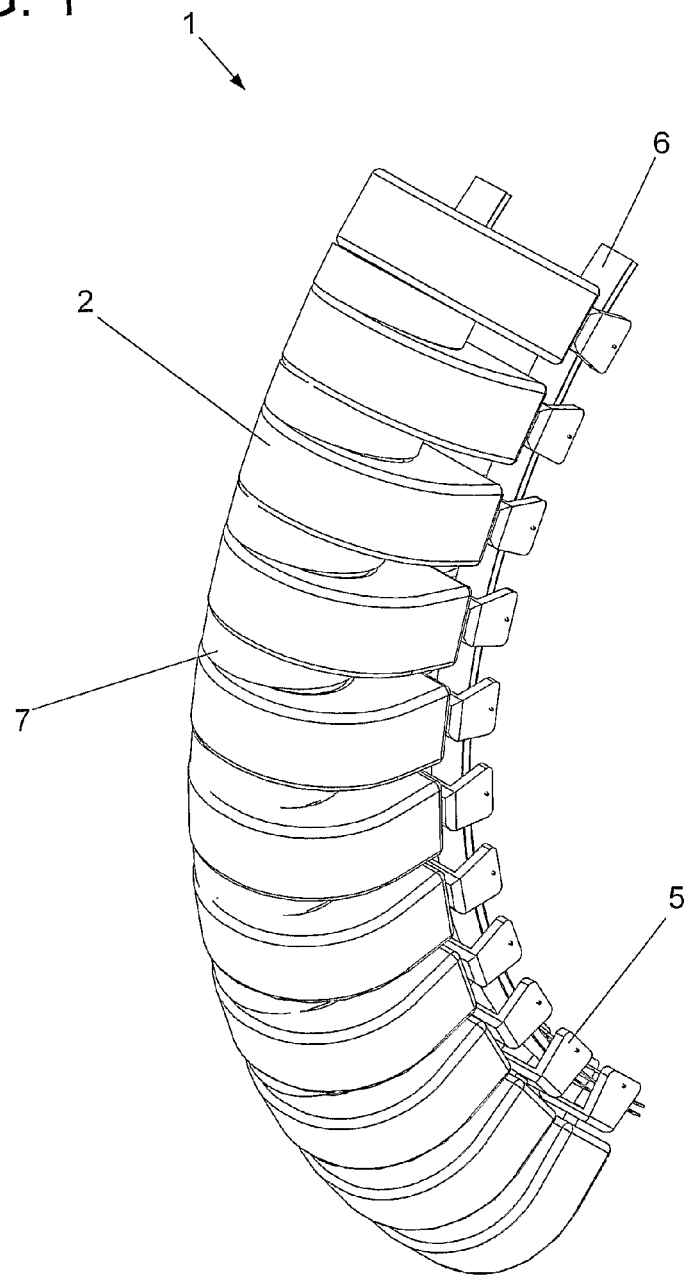
FIG. 1—Shows a view in the posterior perspective of a representation of the vertebral column portion with the new vertebral implant system articulated for the vertebral column stabilization and correction, where it is seen: Articulated vertebral implants (1), vertebral column (2), U-shaped supports or platforms (3), vertebrae (6) lateral portion of the platform or edge (7).
Figure 2:
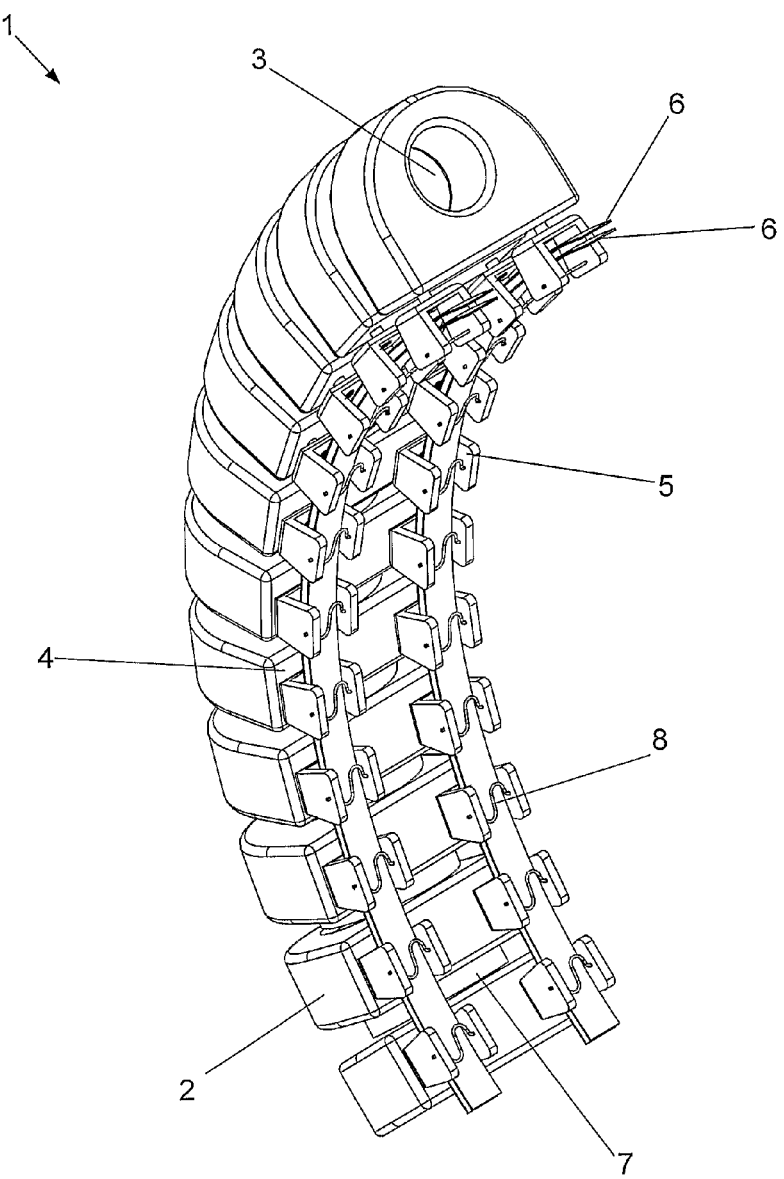
FIG. 2—Shows a view in frontal perspective of a vertebral column portion with the vertebral implants articulated for the stabilization and correction of vertebral deformities where it is seen: vertebral articulated implants (1), vertebral column (2), U-shaped supports or platforms (3), posterior bony portion (5), vertebra (6), lateral portion of the platform or edge (7), flexible blade (8) and S-shaped limiting fastener or "glove".
Figure 3:
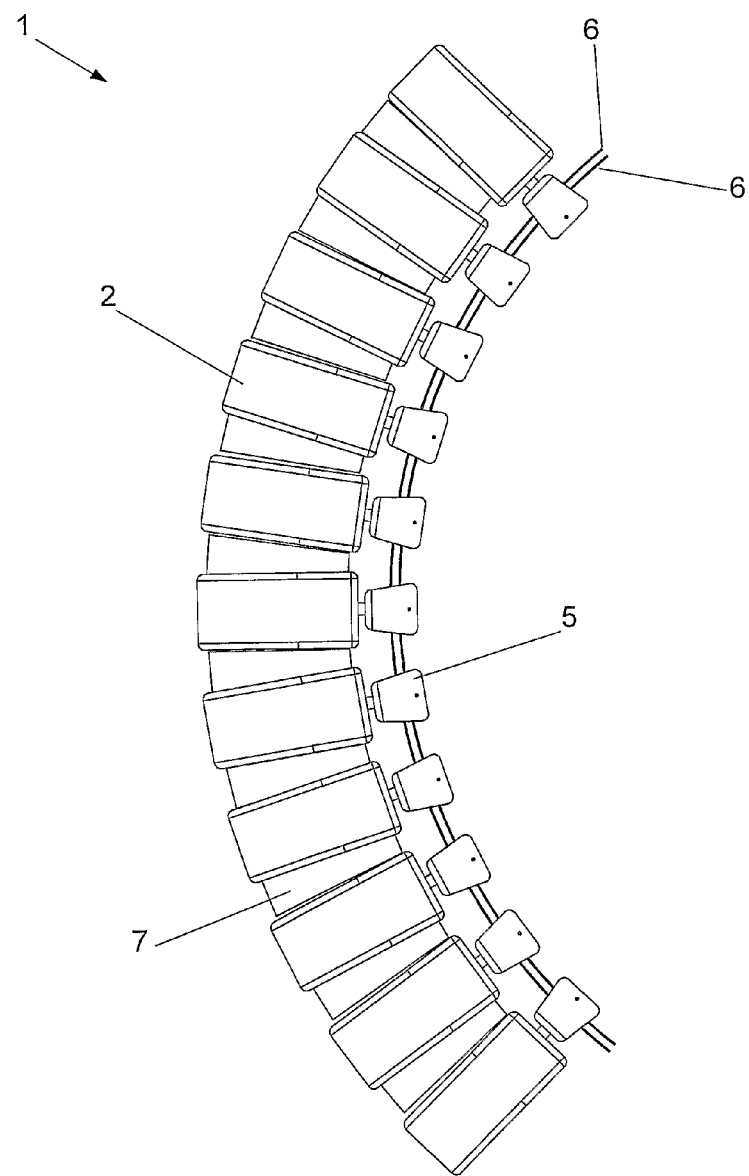
FIG. 3—Shows a view of two representative vertebrae exposing the pedicular screw and the U-shaped support (platform) implants in the posterior bony portion of each vertebra.
Figure 4:
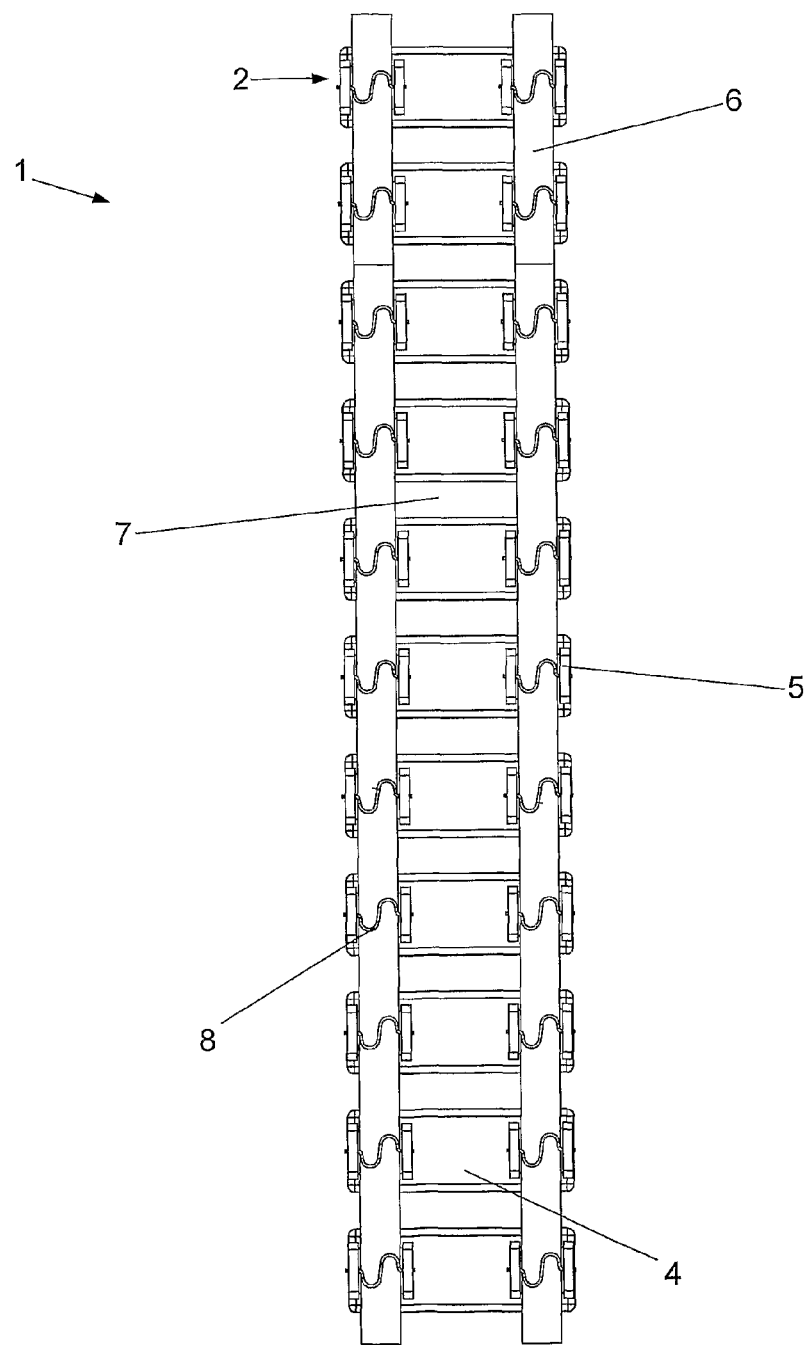
FIG. 4—Shows a lateral view of the representation of a vertebral column portion with the articulated vertebral implants for stabilization and correction of the vertebral column deformities where we see: Articulated vertebral implants (1), vertebral column (2), U-shaped supports or platforms (3), pedicular screw (4), vertebra (6), lateral portion of the platform or edge (7), sliding flexible blades (8).
Figure 5:
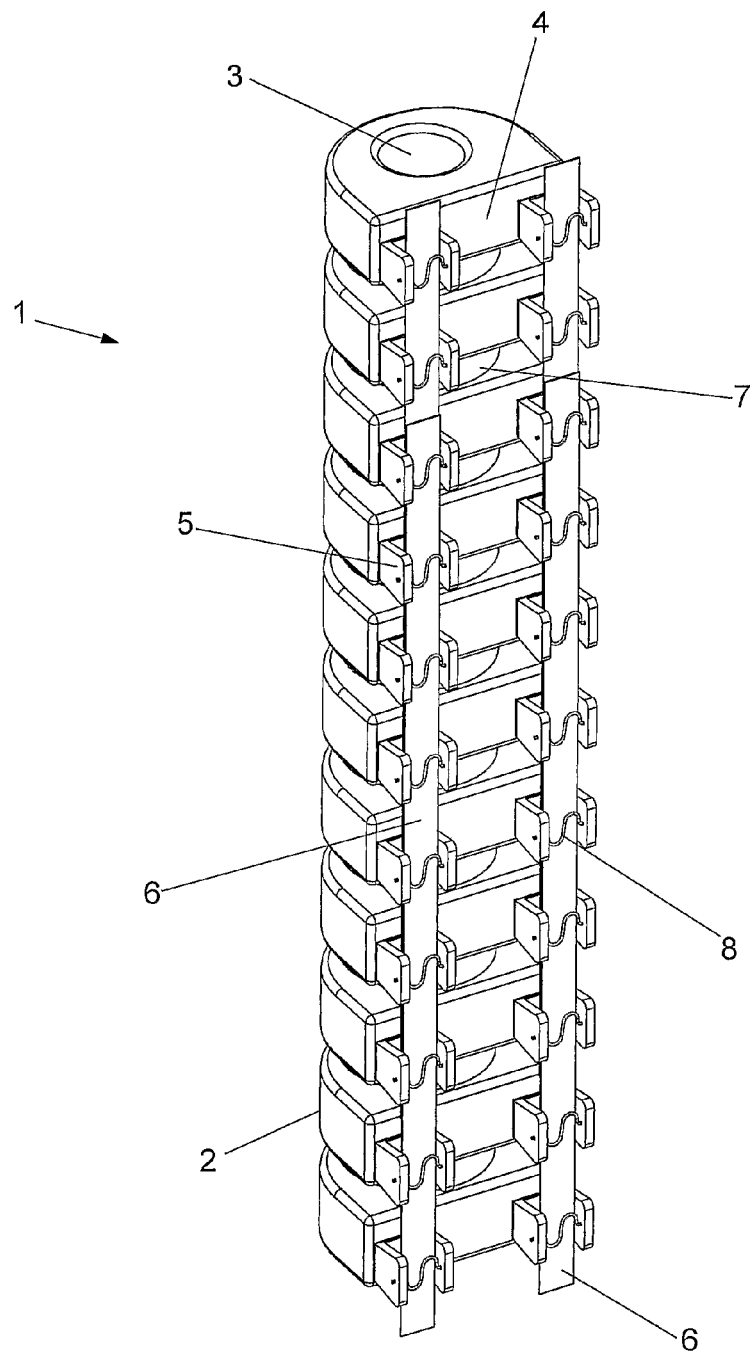
FIG. 5—Shows a view in supero-posterior perspective of the double linear sequence of the vertebral implant's component elements which are articulated to stabilize and correct vertebral deformities, where we can see: articulated vertebral implants (1), U-shaped supports or platforms (3), pedicular screw (4), lateral portion of the platform or edge (7), flexible blade (8), metallic glove or S-shaped lock (10).

According to what the figures above illustrate about how the "FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILIDADES" is constituted by a set of new internal implants for the correction of deformities and/or treatment of the vertebral column (2), denominated articulated vertebral implants (1) which have all levels of natural mobility required for a healthy vertebral column, constituted of two linear parallel sequences of U-shaped supports or platforms (3). The supports or platforms can have other names and geometrical shapes where each pair of the sequence is connected in pedicular screws (4) fixed by penetration, also in parity, in the due posterior bony portion (5) of each vertebra (6) related to the vertebral extension to be implanted.

After assembling the "U"-shaped supports or platforms (3) on the pedicular screws (4) implanted on the vertebrae (6), two thin, continue and flexible metallic blades (8) are coupled between the borders or the lateral portion of the platforms (7)

which belong to each internal track U-shaped support or platform (3), that is, two on each side and one above the other corresponding to each U-shaped linear support sequence (3) in pairs.

The flexible thin blades sets (8) are assembled on the two sides of the vertebral column (2) around the spinal process in such way that the blades' extremities are connected and fixed to the U-shaped terminal support or platform (3).

The inferior flexible thin blades (8) is fixed on the first inferior U-shaped support/platform (3) which corresponds to the first inferior vertebra (6) of the vertebral extension to be implanted, this one bends 180 degrees around a transversal axe which is fixed on the U-shaped support/platform (3). The superior flexible thin blade, then, is fixed on the superior platform of the instrumentation (8). The blade is fixed in a way to be blocked in only one extremity, therefore, with the free internal extremity causing the blades to slide in postural flex condition or any other movement requested to the extension of the implanted vertebral column (2).

Between edges or lateral portion of the platform (7) of each U-shaped support (3) and above the flexible thin blades (8) there is an S-shaped fastener (9) which gives the flexible thin blades (8) condition to lodge safely in the supports/platforms sequence.

Because the flexible thin blades (8) slide mutually one or more rings or metallic lacing or wrapping gloves (10) are estimated to assemble on each blade pair, therefore leading the correct sliding of the free extremities and keeping them to part consequently guiding its movements.

The articulated vertebral implants system (1) application allows the correction of vertebral deformities keeping the vertebral column movements and still allows to keep the vertebral column (2) growth when used in young patients (children and adolescents).

The following items were technically approached: articulated vertebral implants system (1), vertebral column (2), U-shaped supports or platforms (3), pedicular screws (4), posterior bony portion (5), vertebra (6), edges or lateral portion of the platform which have internal tracks for the lodging and sliding of the flexible blades (7), flexible thin blades (8), S-shaped fastener (9), metallic lacing or wrapping gloves (10).

We can, considering the above exposed, come to the conclusion that the "FLEXIBLE, SLIDING, DYNAMIC IMPLANT SYSTEM, FOR SELECTIVE STABILIZATION AND CORRECTION OF THE VERTEBRAL COLUMN DEFORMITIES AND INSTABILITIES" is characterized as a new vertebral implant system which presents, as exposed due to analysis made and by the presented drawings, many differences between the conventional existing models in the orthopedic surgical area for the vertebral column, not to mention technical, functional, constructive characteristics that are completely different from those that belong to the state of the technique.

For offering advantages and for having truly innovative characteristics which fulfill all the originality and novelty requests in the area, the present "FLEXIBLE, SLIDING, DYNAMIC IMPLANT SYSTEM FOR SELECTIVE STABILIZATION AND CORRECTION OF THE VERTEBRAL COLUMN DEFORMITIES AND INSTABILITIES" gathers the necessary and sufficient conditions to deserve the Invention Privilege.

The invention claimed is:

1. A flexible, sliding, dynamic implant system, for selective stabilization and correction of the vertebral column deformities and instabilities, characterized by a flexible, sliding and articulated vertebral implant system applied to a vertebral column and comprising:

two linear parallel sequences of U-shaped supports or platforms, wherein a sequence pair is connected in a poli-axial way to pedicle screws which are fixed by penetration in a posterior bony portion of each vertebra related to a vertebral portion to be implanted;

flexible thin flat blades located between and within the U-shaped supports or platforms in each of the two linear parallel sequences, wherein a width-wise dimension of a cross-section of the flexible thin flat blades is substantially greater than a height-wise dimension of the cross-section of the flexible thin flat blades;

and wherein an S-shaped fastener is located between edges of each U-shaped support or platform and above the flexible thin flat blades;

and wherein the U-shaped supports or platforms are connected with selective poli-axial mobility to the pedicle screws, and are implanted one on each side, or on only one side, of the posterior bony portion of each vertebra related to the vertebral portion to be implanted, and wherein the edges of the U-shaped supports or platforms have internal tracks to receive the flexible thin flat blades.

2. A flexible, sliding, dynamic implant system, for selective stabilization and correction of the vertebral column deformities and instabilities according to claim 1, wherein the flexible thin flat blades are metallic, or made of carbon fiber, or propylene, or polyetheretherketone, and a pair of flexible thin flat blades, one flexible thin flat blade above the other, is connected to each U-shaped support or platform on both sides of the vertebral column.

3. A flexible, sliding, dynamic implant system, for selective stabilization and correction of the vertebral column deformities and instabilities according to claim 1, wherein an inferior flexible thin flat blade is fixed on a first inferior U-shaped support or platform which corresponds to a first inferior vertebra of the vertebral portion to be implanted, and a superior flexible thin flat blade is fixed on a first superior U-shaped support or platform connected to a superior vertebra, and the inferior flexible thin flat blade and the superior flexible thin flat blade are blocked in only one extremity and can slide during a flexion or extension of the vertebral column.

4. A flexible, sliding, dynamic implant system, for selective stabilization and correction of the vertebral column deformities and instabilities according to claim 1, wherein one or more rings or metallic lacing or wrapping gloves are connected to a flexible thin flat blade pair, allowing for the correct mutual sliding of the flexible thin flat blade pair.

5. A flexible, sliding, dynamic implant system, for selective stabilization and correction of the vertebral column deformities and instabilities according to claim 1, wherein a set of articulated vertebral implants corrects vertebral deformities, normalizes growth of the vertebral column, and keeps vertebral anatomic structures intact in children and adolescents.

\* \* \* \* \*